United States Patent [19]

Laguette et al.

[11] Patent Number: 5,578,083
[45] Date of Patent: Nov. 26, 1996

[54] VOICE PROSTHESIS-CARTRIDGE ASSEMBLY

[75] Inventors: Stephen W. Laguette; Edmund V. Seder, both of Santa Barbara, Calif.

[73] Assignee: Helix Medical, Inc., Carpinteria, Calif.

[21] Appl. No.: 559,210

[22] Filed: Nov. 13, 1995

[51] Int. Cl.⁶ ........................................... A61F 2/20
[52] U.S. Cl. ................... 623/9; 623/12; 137/855
[58] Field of Search ............ 623/9, 12; 137/527, 137/855

[56] References Cited

U.S. PATENT DOCUMENTS

| | | | |
|---|---|---|---|
| 4,435,853 | 3/1984 | Blom et al. | 3/1.3 |
| 4,586,931 | 5/1986 | Blom et al. | 623/9 |
| 4,596,579 | 6/1986 | Pruitt | 623/9 |
| 4,614,516 | 9/1986 | Blom et al. | 623/9 |
| 4,773,412 | 9/1988 | Blom | 128/207.14 |
| 4,820,304 | 4/1989 | Depel et al. | 623/9 |
| 4,911,716 | 3/1990 | Blom et al. | 623/9 |
| 5,064,433 | 11/1991 | Blom et al. | 623/9 |
| 5,078,743 | 1/1992 | Mikalov et al. | 623/9 |
| 5,300,119 | 4/1994 | Blom | 623/11 |
| 5,314,470 | 5/1994 | Persson | 623/9 |
| 5,391,205 | 2/1995 | Knight | 623/9 |
| 5,507,809 | 4/1996 | Blom | 623/9 |

FOREIGN PATENT DOCUMENTS 0222509  5/1987  European Pat. Off.  ............... 623/9

*Primary Examiner*—Randy C. Shay
*Attorney, Agent, or Firm*—Marvin E. Jacobs

[57] ABSTRACT

The length of dwelling of a voice prosthesis in the fistula of a patient is extended by supporting the soft hollow body of the prosthesis with an elongated, rigid cartridge and mounting the flapper valve by means of a tab which extends through a slot in the flange of the cartridge. An enlarged cavity in the flange or the body communicates with the slot and receives the leading portion of the tab. The cavity is filled with adhesive to secure the valve to the cartridge.

16 Claims, 3 Drawing Sheets

U.S. Patent   Nov. 26, 1996   Sheet 1 of 3   5,578,083
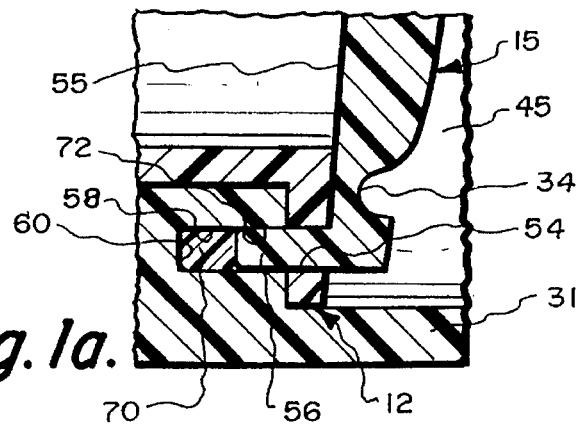
Fig. 1
Fig. 1a.
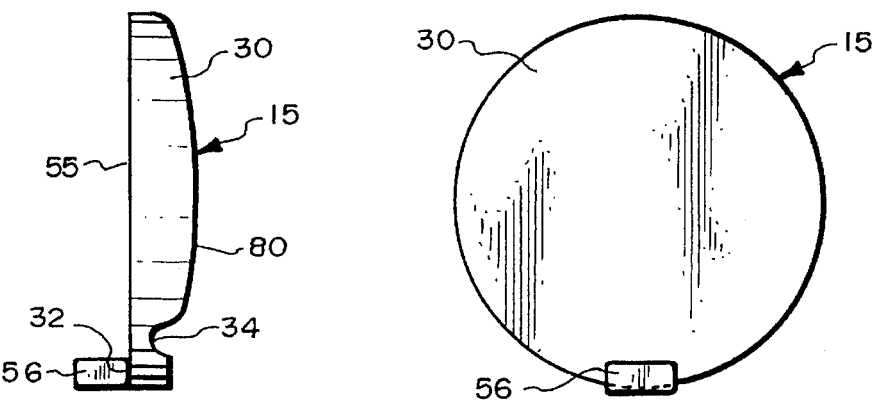
Fig. 2.
Fig. 3.
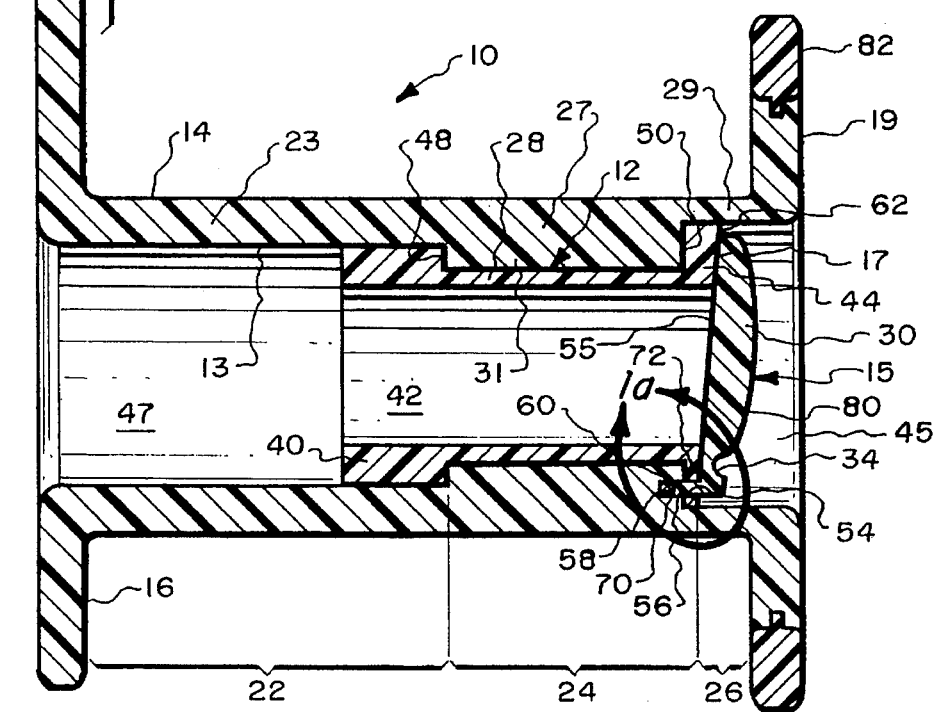

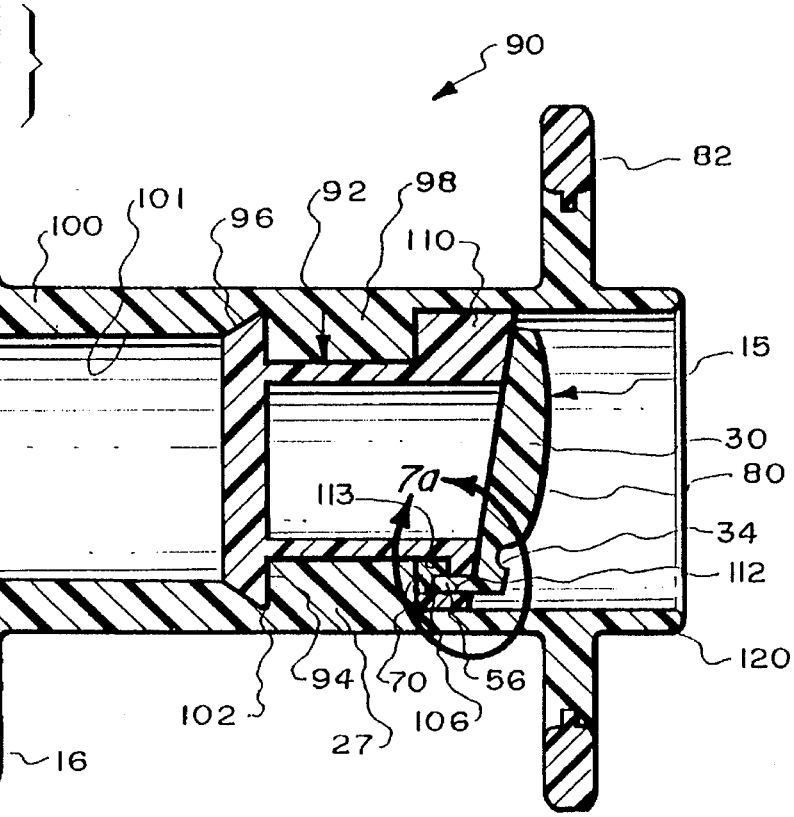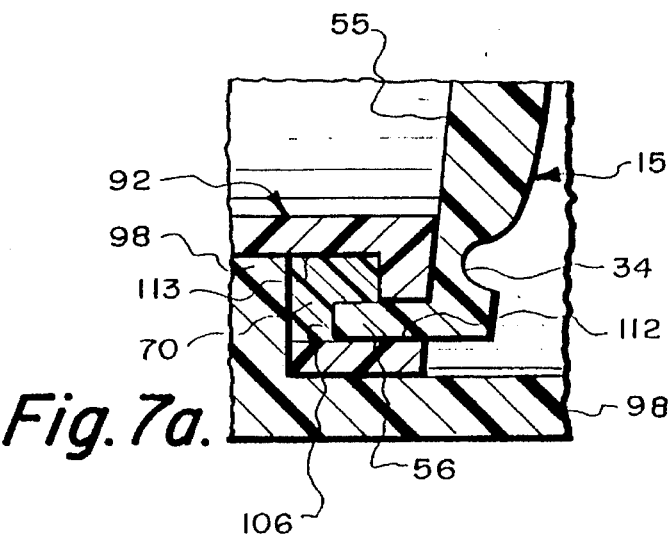

VOICE PROSTHESIS-CARTRIDGE ASSEMBLY

TECHNICAL FIELD

This invention relates to a voice prosthesis and more particularly this invention relates to a type of voice prosthesis developed for patients who can not themselves insert the voice prosthesis such as quadriplegic patients or patients suffering from neurological conditions such as M.S. The voice prosthesis must be inserted by a health care professional.

BACKGROUND OF THE INVENTION

There are several options for restoring speech to patients who have had their larynx removed. One procedure is to surgically create a puncture or fistula between the trachea and the esophagus. A trachea voice prosthesis containing a one-way valve such as a BLOM-SINGER® voice prosthesis is inserted into the tracheoesophageal fistula. The one-way valve protects the airway during swallowing but opens under positive pressure. The voice prosthesis, thus, permits a patient to divert air from the lungs into the esophagus and out through the mouth. Speech is created during passage of air through the upper part of the esophagus.

The prosthesis maintains the fistula open, transfers air from the trachea to the esophagus for voice production and prevents esophageal leakage into the trachea during swallowing. However, the prosthesis being in contact with moisture in a hot, dark environment is subject to growth of commonly found yeast formation, typically Candida Albicans on the valve and the retaining flange. The growth of yeast can interfere with function of the valve and can cause the flange to wrinkle and leak.

The current low pressure voice prosthesis can be removed by the patient every few days and can be replaced with a clean prosthesis. The removed prosthesis is soaked in hydrogen peroxide to remove the layer of yeast from the valve and flange. Some patients however, have difficulty managing frequent removal and reinsertion of the prosthesis. Others, who are physically handicapped are not able to remove, sterilize, or reinsert the prosthesis.

A longer dwelling, low pressure voice prosthesis has been developed that can remain in place in the tracheoesophageal fistula for over 3-4 days, depending on the patient and conditions of use. The patient can confidently use the prosthesis for longer periods. Trips to a health care specialist to remove and replace the prosthesis are greatly extended providing increased comfort and lower cost to the patient.

The flange or collar that rests against the tracheoesophageal wall is strengthened by increasing the thickness and/or diameter of the flange. The stronger flange is more resistant to wrinkling or detachment from the wall. The voice prosthesis can remain in place in the fistula for much longer periods without allowing leakage between the trachea and the esophagus. The stronger and larger collar also reduces possibility of dislodgment of the prosthesis during a coughing or sneezing episode.

However, the thicker and wider flange is more difficult to insert though the fistula and does not reliably seat on the tracheoesophageal wall. An insertion system as disclosed in U.S. Pat. No. 5,300,119, the disclosure of which is incorporated herein by reference, can be utilized to insert the long dwelling voice prosthesis into the fistula. The thicker flange is folded toward the axis of the tube of the prosthesis and inserted into a gelatin capsule, which is inserted through the fistula. Moisture in the esophagus dissolves the capsule which releases the folded flange which is intended to deploy and seat against the tracheoesophageal wall.

Seating of the retention collar against the anterior wall of the esophagus can be confirmed by rotating the inserted prosthesis within the puncture. Correctly and securely inserted prosthesis will rotate freely, repeatedly through 360°. If the prosthesis does not rotate freely, it suggests that the retention collar has not unfurled and seated. The flange does not fully open and seat in every instance. The body of the prosthesis may be too short or a portion of the flange may be caught in the fistula. A system for radiographic assessment for direct confirmation that the prosthesis is correctly seated is disclosed in copending application Ser. No. 08/282, 277 filed on Jul. 27, 1994, the disclosure of which is expressly incorporated herein by reference.

Yeast growth on the valve can also cause distortion of the shape of the valve or form wrinkles in the body of the valve which prevents the valve from closing.

Leaking also appears to be due to distortion of the valve body adjacent to the seat of the valve and to yeast growth on the seat. Forming the valve with an arcuate dome shape increased resistance to folding or bending of the valve. However, some valves still leaked after extended placement in a fistula.

DESCRIPTION OF PRIOR ART

U.S. Pat. No. 5,314,470 discloses a soft voice prosthesis which includes a stiffening ring 14 inserted into a groove in the body of the prosthesis. Though the ring stiffens the body adjacent the valve it does not prevent distortion of the body by muscular movement or distortion of the valve by growth of yeast. The valve is thin, it is not dome shaped and is not pre-loaded. It will readily distort when a layer of yeast grows on its surface. Furthermore, the flap valve is attached to the soft body with a segment that remains after cutting the valve from the body. This is a labor intensive step and the thin segment does not provide a secure and reliable attachment of the valve to the prosthesis. If the segment should sever, the valve can fall into the lungs of the user.

STATEMENT OF THE INVENTION

A voice prosthesis having the ability to have a more extended dwell in a fistula of a patient is provided by the invention. The prosthesis is stronger, more reliable and is simple to manufacture and insert into a patient. The valve in the prosthesis of the invention does not leak. It remains seated and seated to the valve seat even after extended wear and fouling by growth of yeast on its surface.

The attachment of the valve to the seat is provided by a tab integrally molded to the valve. The tab is disposed normal to the valve within the periphery of the valve. The tab is received in a slot in a cartridge support structure and is adhered to the prosthesis by adhesive received in a recess behind the slot in the cartridge. The valve attachment is extremely secure and is not likely to detach or fail due to fatigue. The hard, smooth surface of the end face of the cartridge can function as the seat for the valve.

The valve is preferably pre-loaded onto the seat by providing the seat with a slanted face with the upper portion of the face rearward of the lower portion of the face containing the slot for attachment of the valve. The valve may optionally be dome shaped to provide further strengthening of the valve and to assure that it will not distort and leak even when encrusted with a layer of yeast.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is a view in section of the assembly of the valve, cartridge and body to form a first embodiment of a voice prosthesis;

FIG. 1a is an enlarged sectional view of FIG. 1 for purposes of clarity;

FIG. 2 is a side view in elevation of a valve for use in the voice prosthesis of the invention;

FIG. 3 is a front view in elevation of the valve shown in FIG. 1;

FIG. 7 is a view, partially in section, of the assembly of the body, valve and cartridge of the second embodiment of a voice prosthesis; and FIG. 7a is an enlarged sectional view of FIG. 7 for purposes of clarity.

DETAILED DESCRIPTION OF THE INVENTION

Figure 4:
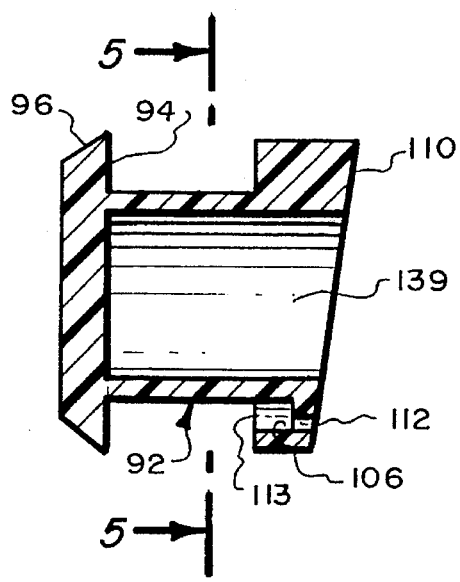
FIG. 4 is a view in section of a second embodiment of a cartridge.

Referring now to FIGS. 1 and 1a, the voice prosthesis 10 of the invention is formed of a tubular body 14 a hollow, rigid cartridge 12 received in the channel 13 through the body 14 and a flapper valve 15 mounted on the rear face 17 of the cartridge 12.

A front tracheal flange 16 and a rear retention esophageal flange 19 are connected to the ends of the body 14. A flexible tab 18 can be attached to the front flange 16. The tad 18 can contain an aperture 20 which can be connected to an insertion tool, not shown. The body 14, front flange 16 and rear flange 19 are preferably a single molded, unitary structure formed from a biocompatible elastomer such as silicone resin, suitably a 50 durometer, medical grade, silicone elastomer. Since the resin is transparent and the prosthesis structure is small, the prosthesis is difficult to visualize and handle. Therefore, the molding resin generally contains a small amount, from 0.1 to 0.5% of a biocompatible pigment to aid in seeing the device. The pigment can be a heavy metal salt such as barium sulfate. The cartridge 12 is formed of an inert, self-lubricating polymer, suitably a fluorinated resin such as TEFLON (polytetrafluoroethylene) or a polyalkylene resin such as polyethylene or polypropylene.

The tubular body 14 has a first section 22 having a wall 23 of a first thickness, a central section 24 having a wall 27 of a greater thickness and a third wall section 26 having a wall 29 of reduced thickness. The central wall section 24 forms a cylindrical boss 31 which is received in an annular channel 28 formed in the outer wall of the cartridge 12.

The hollow cartridge 12 has a long front flange 40, a narrow rear flange 44 forming the central channel 42 between the flanges 40, 44. The cartridge 12 is assembled with the body 14 by inserting the front flange 40 of the cartridge 12 into the rear opening 45 of the channel 47 through the body 14 and forcing it through the central channel 47 of the body compressing the boss 31 until the front flange 40, enters the central channel 47. The front flange 40 seats against the end wall 48 of the boss 31 and the rear flange 44 seats against the rear wall 50 of the boss 31. The length of the cartridge is at least 30% of the body.

Referring now to FIGS. 2 and 3, the rear flange 44 has a horizontal slot 54 for receiving a tab 56 mounted on the front face 55 of the valve 15. The rear face of the boss 31 can have a recess 58 in alignment with the slot 54 for receiving the tab 56. The remaining volume 60 in the recess 58 is filled with biocompatible adhesive such as a silicone adhesive. The rear face 62 of the rear flange 44 can be angled 1°–10°, usually 3°–7°, to the vertical in order to preload the valve 15.

Referring further to FIGS. 2 and 3, the flapper valve 15 has a round segment 30 connected to an attachment flap 32. A live hinge 34 in the form of a score line separates the segment 30 from the flap 32. A tab 56 is provided on the flap 32 for attaching the valve 15 to the body of the prosthesis 10. The recess 58 is filled with adhesive 70. The tab 56 is inserted through the slot 54 in the flange 44 into the adhesive filled recess 58. Excess adhesive 70 flows out of the recess 58 and forms a film 72 behind the flap 32 adhering the flap 32 to the opposing face 62 of the flange 44.

The broad tab 56 snugly received in the elongated slot 54 and potted with adhesive 70 in the recess 58 forms a strong, reliable bond. The elongated adhesive line restricts bending to the hinge line 34 on the valve. The hinge is located on the lower, recessed portion of the rear face of the flange 44 and preloads the valve 15. The valve is further strengthened by the increased thickness of the dome-shaped rear face 80 of the round segment 30. Leakage of the valve is further decreased due to the seating of the valve element 30 on the hard, smooth outer surface 17 of the rear flange 44 of the cartridge.

In order to assure that the rear flange 19 of the body 14 is fully seated on the esophageal wall surrounding a fistula, a narrow opaque ring 82 can be attached to or molded into the rear flange 19 as disclosed in copending application, Ser. No. 08/282,277 filed Jul. 27, 1994, the disclosure of which is expressly incorporated herein by reference.

The ring 82 has a width at least 10% the diameter of the rear flange 19 usually from 10% to 50% the diameter of the annular rear flange. Usually the rear flange 19 has a diameter of about 0.5 inch and the ring has a width of about 0.05 to 0.10 inch. The ring 82 preferably has an outer perimeter coincident with that of the rear flange 19 so that folds anywhere on the rear flange will be detected by the displayed image of the ring 82. The ring is preferably formed of the same flexible resin as the rear flange but contains an amount of radiopaque pigment such as barium sulfate sufficient to render the ring opaque to X-rays. Usually the pigment is present in an amount from at least 5% to 35%, generally around 20% by weight.

Figure 5:
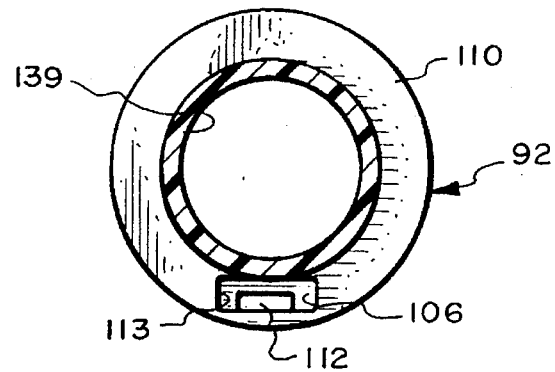
FIG. 5 is a view in section taken along line 5—5 of FIG. 4.
Figure 6:
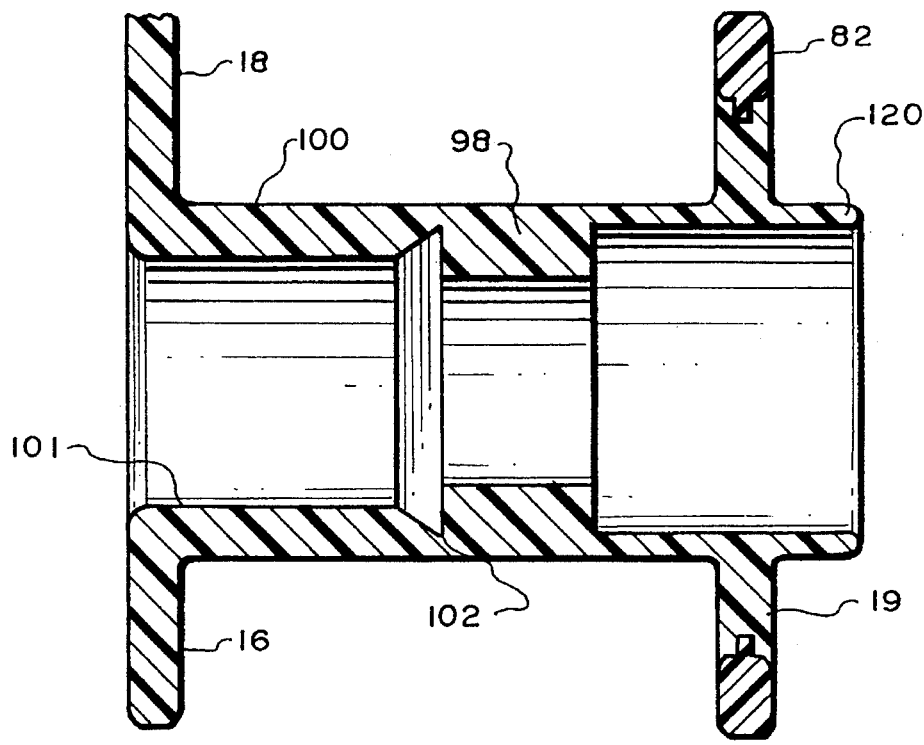
FIG. 6 is a view in section of a body of the second embodiment of the prosthesis of the invention.

Another embodiment is illustrated in FIGS. 4–7. The voice prosthesis 90 contains an improved cartridge 92. The front flange 94 of the cartridge 92 has a bevel 96 so that it is easier to move the front flange 94 past the boss 98 on the body 100 of the device. A groove 102 may be provided in the inner wall 101 of the body 100 adjacent the front of the boss 98. The groove 102 preferably has a beveled front face to receive and lock the flange 94 as it snaps into the groove 102. The boss 98 seats between the flanges 94 and 110 and the wall segment 139 of the cartridge 92.

Another feature of the cartridge 92 of the invention is the placement of the adhesive cavity 106 in the rear of the rear flange 110 such that it communicates with the slot 112. The valve 15 and cartridge 92 can be preassembled before the cartridge is inserted into the flexible body 100. The tab 56 is inserted through slot 112 in the flange 110 into the cavity 106. Adhesive 70 can be placed into the cavity from the rear opening 113 of the cavity 106. There is no need for a cavity in the flexible body which would weaken the body and could provide a site for failure during flexure of the soft elastic body adjacent the hard flange.

The body 100 can also contain an elongated hood 120 placed rearward of the rear flange 110 to further protect the valve 15 from failing.

The Indwelling Low Pressure Voice Prosthesis of the invention is designed for those persons who are unable or resistant to changing the voice prosthesis every two or three days as was recommended for the non-indwelling, patient-removable Low Pressure Voice Prosthesis. The Indwelling Low Pressure Voice Prosthesis has been specifically designed to maintain the placement of the prosthesis in the tracheoesophageal puncture so that routine changing of the device is not necessary.

The Indwelling Low Pressure Voice Prosthesis is loaded into a gelatin capsule, using a gel cap loading tool. The gel cap provides a smooth, rounded shape to the tip end of the voice prosthesis, thus enabling easier entry into the tracheoesophageal puncture when placed by the clinician.

The prosthesis is placed in the fistula by inserting the strap of the voice prosthesis into the center hole on the top side of the gel cap loading tool and gently pulling the prosthesis down and through this opening until the rear esophageal flange is positioned over this center hole.

The tubular portion of the voice prosthesis is grasped and the prosthesis is very slowly pulled down further, such that the rear flange on the tip of the voice prosthesis begins to fold forward inside the center hole. Over-pulling will cause the voice prosthesis to be pulled completely through the loading device. The gel cap is placed over the center hole in the loading tool and into the groove, such that it is securely in place. A fingertip is placed on the tip of the gel cap while simultaneously pushing the voice prosthesis back up through the center hole and out of the loading device. The prosthesis is pushed gently until the folded, rear flange is fully residing in the gel cap. The pushrod provided with the gel cap loading tool may be used to push the device through from the back.

The gel cap-tipped end of the voice prosthesis is gently grasped and the prosthesis is carefully pulled the rest of the way back up through the loading device. The prosthesis is placed on the inserter, and the strap attached over the safety peg, as shown in U.S. Pat. No. 5,064,433, the disclosure of which is expressly incorporated herein by reference. The position of the gel cap on the tip of the voice prosthesis is inspected to assure that it is securely and fully encapsulating the rear flange.

A light coating of water or water-soluble lubricant (oil-free) is applied to the tip of the gel-capped end of the voice prosthesis and the voice prosthesis is immediately inserted fully into the tracheoesophageal puncture by aligning the tip of the voice prosthesis partially in the puncture with the neck strap oriented upwards. The prosthesis is held in this position of full insertion for at least 3 minutes. This allows time for the gel cap to dissolve and release the retention collar within the esophagus.

If the prosthesis does not insert easily on the first attempt, do not continue to try to insert. Instead, a clean 22 French tracheoesophageal dilator is inserted for a few minutes to dilate the pathway.

The voice prosthesis strap is detached from the safety peg on the inserter. A finger is placed against the strap and the inserter is carefully withdrawn from the prosthesis with a twisting motion. A piece of tape is placed over the voice prosthesis strap against the skin.

The Indwelling Low Pressure Voice Prosthesis of the invention is designed to permit optional detachment of the strap by a physician or trained speech pathologist following confirmation that the rear flange on the prosthesis is fully opened and securely positioned.

The rear flange emerges from the dissolved gel cap and unfurls within the esophageal lumen. Seating of the rear flange against the anterior wall of the esophagus, can be confirmed by rotating the inserted prosthesis within the puncture while it is attached to the inserter. A correctly and securely inserted prosthesis will rotate freely. Rotate the prosthesis repeatedly 360°. Slight resistance may be detected on the first rotation because of residual gelatin that has not completely dissolved. Allow at lest three minutes for the gel cap to dissolve following prosthesis insertion before proceeding with the rotation confirmation procedure. A voice prosthesis that does not rotate freely suggests that the rear flange has not unfurled and seated within the esophageal lumen. Assessment of the position of the rear flange of the prosthesis is recommended for direct confirmation/assessment.

Removal of the Indwelling Low Pressure Voice Prosthesis should only be done by grasping the outer rim of the device securely with a hemostat. Pull gently and firmly until the prosthesis is fully withdrawn. Insert a 22 French dilator and tape it into position for five minutes prior to inserting a new Indwelling Low Pressure voice Prosthesis that has been attached to an inserter. Never remove one voice prosthesis and reinsert another voice prosthesis without first dilating the tracheoesophageal puncture with the 22 French dilator. Always use a gel cap on the tip of an Indwelling Low Pressure Voice Prosthesis to enable easy, atraumatic insertion.

The Indwelling Voice Prosthesis may be left in place in the tracheoesophageal puncture until it ceases to function correctly, that is, until it leaks or is not providing adequate voice for speech. If the prosthesis is not functioning properly, the patient should return to the clinician for evaluation.

The Blom-Singer Flushing Pipet provides a means for flushing small particulate matter from the lumen and valve member of the Blom-Singer Indwelling Low Pressure Voice Prosthesis while in-situ, i.e., in the user's tracheoesophageal puncture. The following instructions should be made clear to the patient as part of the routine care of the Blom-Singer Indwelling Low Pressure Voice Prosthesis.

The patient should illuminate the tracheostoma with a bright light source such that the open end of the voice prosthesis is clearly visible. Use long handled forceps (tweezers) to carefully remove any dried debris (phlegm) that may be in the open end of the voice prosthesis.

Fill approximately one third of the stem of the pipet with clean water. Carefully and gently insert the tip of the pipet into the voice prosthesis only until it abuts against the stopper on the stem of the pipet. Briskly squeeze the bulb on the piper to flush a rapid squirt of water through the voice prosthesis. If liquid will not readily squirt through the voice prosthesis, this indicates that it may be plugged with dried phlegm. Allow a few drops of water to dissolve this dried matter for a few minutes and then re-flush with the pipet until the debris breaks free. The debris must be removed from the tracheoesophageal puncture with a hemostat by the clinician for thorough cleaning. Never attempt to reinsert an Indwelling Low Pressure Voice Prosthesis that has the strap removed.

After flushing, remove the piper carefully to avoid dislodging the voice prosthesis. Inspect the interior of the voice prosthesis with a bright light. Repeat flushing as needed.

If the voice prosthesis is accidently dislodged from the puncture, the patient should be instructed to immediately place a 22 French dilator in the puncture to keep the puncture from closing. The patient should then return to his/her clinician for re-insertion of the voice prosthesis.

It is to be realized that only preferred embodiments of the invention have been described and that numerous substitutions, modifications and alterations are permissible without departing from the spirit and scope of the invention as defined in the following claims.

We claim:

1. A voice prosthesis for insertion into a fistula in a tracheoesophageal wall of a patient comprising in combination:

a hollow, annular, flexible body to be disposed in and to maintain said fistula open, said body having a first tracheal end and a second esophageal end;

a first flange connected to the first end of the body;

a second flange attached to the second end of the body;

an elongated, hollow, rigid, cartridge received in said body between said ends having an annular wall terminating in a tracheal face and an esophageal face;

means for retaining said cartridge in said body; and means on said esophageal face for mounting a flapper valve.

2. A voice prosthesis according to claim 1 further including means for seating said valve said means comprising the esophageal face of the cartridge.

3. A voice prosthesis according to claim 1 in which the esophageal face of the cartridge is disposed between the second flange and the first flange.

4. A voice prosthesis according to claim 3 in which the esophageal face of the cartridge has a surface angle from 1 to 10 degrees from vertical.

5. A voice prosthesis according to claim 4 in which said angle is 5 degrees.

6. A voice prosthesis according to claim 1 in which the esophageal face of the cartridge is disposed at an angle to the longitudinal axis of the cartridge with a first portion of the esophageal face of the cartridge disposed closer to the first flange than the remaining portion of the esophageal face of said cartridge.

7. A voice prosthesis according to claim 6 in which said mounting means is present on said first portion.

8. A voice prosthesis according to claim 7 in which the mounting means comprises an axial slot in said rearward portion for receiving a tab projecting from said valve.

9. A voice prosthesis according to claim 8 in which said cartridge comprises a central section connected to a first flange and to a second flange, the outer surface of the second flange forming said esophageal face and said slot penetrating said second flange.

10. A voice prosthesis according to claim 9 in which the body contains a recess facing said slot, said tab enters a portion of said recess and the remainder of the recess contains adhesive.

11. A voice prosthesis according to claim 9 in which an outer cylindrical recess disposed on the central section of the cartridge is formed between the first flange and the second flange and said retaining means includes a boss formed on the inner surface of the hollow body and said boss is received in said recess.

12. A voice prothesis according to claim 11 in which the second flange of the cartridge has an outer diameter larger than the diameter of the first flange of the cartridge.

13. A voice prosthesis according to claim 11 in which the face of the first flange which faces the tracheal end contains a chamfer.

14. A voice prosthesis according to claim 1 in which the second flange of the cartridge includes a cavity connected to said slot.

15. A voice prosthesis according to claim 1 in which the length of the cartridge is at least 30% the length of the body.

16. A voice prosthesis according to claim 1 further containing a flapper valve.

* * * * *